United States Patent [19]

Umezawa et al.

[11] 4,185,156
[45] Jan. 22, 1980

[54] PEPTIDES AND ACID ADDITION SALTS THEREOF

[75] Inventors: Hamao Umezawa, Tokyo; Takaaki Aoyagi, Fujisawa; Tomio Takeuchi, Tokyo; Tetsushi Saino, Yono; Michinori Koyama, Tokyo, all of Japan

[73] Assignee: Zaidan Hojin Biseibutsu Kagaku Kenkyu Kai, Tokyo, Japan

[21] Appl. No.: 942,581

[22] Filed: Sep. 15, 1978

[30] Foreign Application Priority Data

Sep. 21, 1977 [JP] Japan ................. 52-112568

[51] Int. Cl.² ............... C07C 101/72; A01N 9/20
[52] U.S. Cl. ...................... 562/440; 424/319
[58] Field of Search ............ 562/440, 443, 444; 260/112.5 R

[56] References Cited

U.S. PATENT DOCUMENTS

| 4,052,449 | 10/1977 | Umezawa et al. | 260/112.5 R |
| 4,073,892 | 2/1978 | Okamoto et al. | 260/112.5 R |
| 4,087,520 | 5/1978 | Braun et al. | 260/112.5 R |

FOREIGN PATENT DOCUMENTS 1510470  5/1978  United Kingdom ............. 260/112.5 R

OTHER PUBLICATIONS

Umezawa et al., J. of Med. Chem., vol. 20, #4, pp. 510-516, (1977).

Primary Examiner—James H. Reamer
Attorney, Agent, or Firm—Herbert W. Taylor, Jr.

[57] ABSTRACT

The compounds of this invention represented by the following formula:

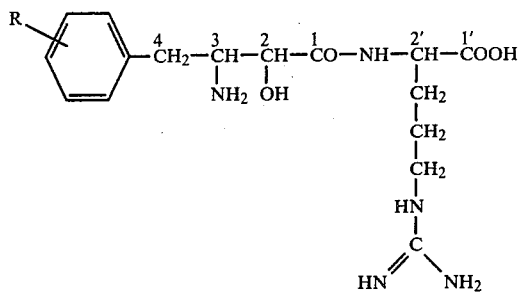

(wherein R is hydrogen atom, an alkyl group having $C_1$ to $C_4$, a hydroxy group or a halogen atom) can be obtained by condensing the compounds represented by the following formula:

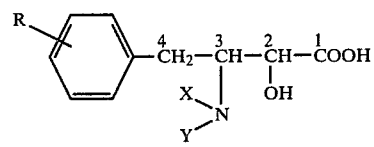

wherein R is as defined above, X is hydrogen atom, and Y is hydrogen atom or an amino protecting group or reactive derivatives thereof with (S)-arginine according to a method commonly employed in the peptide chemistry.

The peptides according to this invention have strong inhibitory activity against aminopeptidase B, can raise immunity of the organisms and prove useful for inhibiting transfer of cancer and relapse thereof. Also, when used jointly with Bleomycin which is an antitumor agent, they can greatly enhance the antitumor effect of said agent.

5 Claims, No Drawings

PEPTIDES AND ACID ADDITION SALTS THEREOF

BACKGROUND OF THE INVENTION

1. Field of the Invention

This invention relates to chemical compounds of the peptide type produced by synthetic methods and includes various processes.

2. Description of the Prior Art

Umezawa et al. have previously succeeded in isolating Bestatin [(2S, 3R)-3-amino-2-hydroxy-4-phenylbutanoyl-(S)-leucine] having a strong inhibitory activity against aminopeptidase B, leucine aminopeptidase and Bleomycin hydrolase from the culture of Bestatin-producing fungus belonging to the actinomyces. See, for example, U.S. Pat. No. 4,029,547 and J. Antibiotics, 29, 97–103 and 600–601 (1976).

Taking note of the excellent physiological activities of Bestatin, the present inventors have made researches into the method for synthetic preparation of this compound and novel peptides having similar structure to Bestatin and considered to possess the same physiological activities as Bestatin, and succeeded to synthesize Bestatin and its analogous compounds represented by the following general formula:

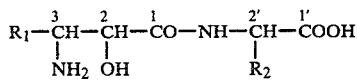

wherein $R_1$ is a lower alkyl group, cycloalkanoalkyl group, phenyl group, benzyl group or substituted benzyl group, and $R_2$ is an alkyl group having 1 to 6 carbon atoms, hydroxyalkyl group, mercaptoalkyl group, carboxyamidoalkyl group, alkoxyalkyl group, alkyl mercaptoalkyl group, carboxyalkyl group, aryl group, aralkyl group or substituted aralkyl group. See, for example, U.K. Pat. No. 1,510,477 and J. Medicinal Chemistry 20(4), 510–515 (1977).

SUMMARY OF THE INVENTION

There is provided by the present invention the peptides represented by the following formula (I):

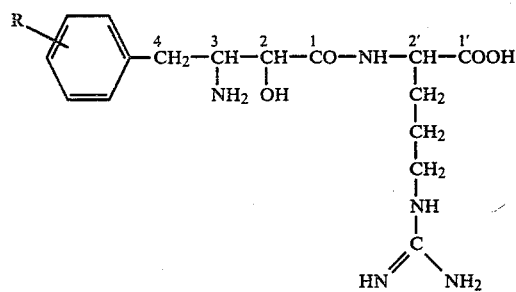

wherein R is hydrogen atom, a hydroxy group, an alkyl group having 1 to 4 carbon atoms, or a halogen atom and pharmaceutically acceptable acid addition salts thereof and a process for their preparation.

The pharmaceutically acceptable salts include the organic and inorganic acid addition salts, for example, those prepared from acids such as hydrochloric, sulfuric, sulfonic, tartaric, fumaric, hydrobromic, hydroiodic, glycolic, citric, maleic, phosphoric, succinic, acetic and the like. Such salts are prepared by conventional methods by reacting the free base with the desired acid. The compounds of this invention contain a multiplicity of salt forming groups and any or all of them can be combined with one or more acids to form acid salts.

The present inventors have made further researchers and synthesized the peptides represented by the above-shown formula (I) and acid addition salts thereof, and the results of the tests of the inhibitory action of these compounds against aminopeptidase B revealed the surprising fact that these compounds have as much as about 3 to 20 times as high inhibitory effect as Bestatin. It was thus discovered that because of their strong aminopeptidase B activity, the compounds of this invention can inhibit generation of bradykinin to produce an antiphlogistic action and hence are usable as remedial medication for various diseases. It was also found that the compounds of this invention have strong inhibitory action against leucine aminopeptidase as well as hydrolase of Bleomycin and can also act as an adjuvant for enhancing the carcinostatic action of Bleomycin.

As a result of further studies on utility of the peptides of this invention for medicinal applications, the present inventors learned that these peptides are useful for elevating immunity of the organisms and for preventing transfer of cancer and its relapse, and that when used as an adjuvant in Bleomycin or other compounds currently used as anti-cancer drugs, they can greatly enhance the carcinostatic effect of these compounds.

The present invention was completed on the basis of these findings.

The invention is now described in detail.

For synthesizing the object compounds (I) of this invention, (2S, 3R)- and (2RS, 3RS)-amino acids represented by the following formula (II):

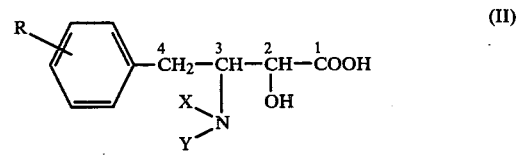

wherein R is as defined above, X is hydrogen atom, and Y is hydrogen atom or an amino protecting group or reactive derivatives thereof and (S)-arginine are condensed according to an ordinary peptide bonding method and then, if necessary, said protecting group is eliminated.

(2S, 3R)- and (2RS, 3RS)-amino acids represented by the above-shown formula (II) can be obtained by hydrolyzing nitrile derivatives represented by the following formula (III) with an acid:

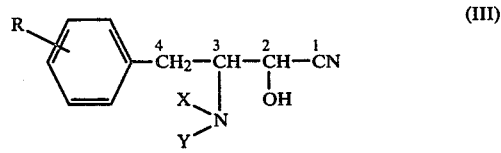

wherein R, X and Y are as defined above.

Any known type of amino protecting groups commonly employed in the peptide chemistry may be used as the amino protecting group in the compounds of the formula (II) and (III), but as preferred examples of such protecting groups the following may be cited: acyl type protecting groups: formyl, acetyl, trifluoroacetyl, and substituted or non-substituted benzoyl such as benzoyl, nitrobenzoyl or tolyl; urethane type protecting groups: substituted and non-substituted benzyloxycarbonyl such as benzyloxycarbonyl, methoxybenzyloxycarbonyl, nitrobenzyloxycarbonyl or halogenobenzyloxycarbonyl, alkoxycarbonyl having 1 to 6 carbon atoms, and cycloalkanoxycarbonyl; other protecting groups: substituted and non-substituted arylsulfonyl such as benzenesulfonyl, methoxybenzenesulfonyl, nitrobenzenesulfonyl, toluenesulfonyl or naphthalenesulfonyl: o-nitrophenylsulphenyl and trityl.

The carboxyl group of arginine may or may not be protected. Any known carboxyl-protecting group used in the peptide chemistry may be employed in this invention. Most preferred among these protecting groups are alkyl group having 1 to 4 carbon atoms, phenyl group, substituted phenyl group such as halogenated or nitrated phenyl group, benzyl group, and substituted benzyl group such as methoxyphenyl or nitrobenzyl group. For protection of the guanidine group, proton and other generally employed protecting groups such as nitro group and tosyl group may be used.

Various methods are available for condensing (2S, 3R)- and (2RS, 3RS)-amino acids represented by the formula (II) and (S)-arginine, and among such methods are a carbodiimide method wherein dicyclohexylcarbodiimide or 1-ethyl-3-(3-dimethylaminopropyl)-carbodiimide is used; an azide method using hydrazide; a mixed acid anhydride method employing ethyl chloroformate or isobutyl chloroformate; an active ester method employing cyanomethyl ester, vinyl ester, substituted and non-substituted phenyl esters, thiophenyl ester or hydroxysuccinimide ester; an O-acyl hydroxylamine derivative method employing acetoxime or cyclohexanoneoxime; and N-acyl compound method employing carbonyldiimidazole or the like.

Solvents usually used for peptide bonding may be employed in the above condensation reaction. Such solvents include ethers such as diethylether, tetrahydrofuran and dioxane, esters such as ethyl acetate, ketones such as acetone and methyl ethyl ketone, halogenated hydrocarbons such as methylene chloride and chloroform, amides such as dimethylformamide and dimethylacetamide, and nitriles such as acetonitrile.

In case a compound of the general formula (II) whose amino group is protected and (S)-arginine whose carboxyl group is not protected are condensed according to the azide method or active ester method, it is preferred to perform the condensation reaction in the presence of an inorganic base such as sodium bicarbonate or magnesium oxide or an organic tertiary base such as triethylamine or N-methylmorpholine by using an organic solvent miscible with water.

The protecting groups in the resulting protected compounds may be removed by a usual method employed in the peptide chemistry such as catalytic reduction using palladium as catalyst, hydrogen bromide in acetic acid, trifluoroacetic acid, hydrogen chloride in an organic solvent, an alkali saponification, or treatment with metallic sodium in liquid ammonia or liquid hydrogen fluoride. This gives the object product represented by the formula (I).

The physiological activities of the compounds (I) of this invention were determined as follows:

(A) Inhibitory activity against aminopeptidase B

Testing method:

A modified version of the Hopsu et al. method (V. K. Hopsu, K. K. Makinen and G. G. Glenner, Archives of Biochemistry and Biophysics 114, 557 (1966)) was used for determining the aminopeptidase B activity. A mixed solution (pH 7.0) prepared by adding 1.0 ml of 0.1 M tris-hydrochloride buffer and 0.7 ml of a solution containing the specimen to 0.3 ml of 0.1 mM arginine-$\beta$-naphthylamide was heated at 37° C. for 3 minutes and then added with 0.2 ml of an aminopeptidase B solution purified by using Sephadex G-100 (trademark for gelfiltrant composed of dextran derivative, manufactured by Pharmacia Fine Chemicals Inc.) according to the enzyme purification method of Hopsu et al. After 30-minute reaction at 37° C., 0.6 ml of 1.0 M acetate buffer (pH 4.2) containing Garnet GBC (o-aminoazotoluene diazonium salt) in concentration of 1.0 mg/ml and Tween 20 in concentration of 1.0% was added, and allowing the mixture to stand at room temperature for 15 minutes, absorbance (a) at 530 nm was measured. There was also measured absorbance (b) of the control using the buffer solution not containing the specimen. The aminopeptidase B inhibition percent was calculated from (b-a)/b × 100.

Results:

Inhibition percentages at various specimen concentrations were measured according to the above-said testing method, and 50% inhibition ($ID_{50}$) was induced therefrom. The results are shown in Table 1.

Table 1

| | Compound | $ID_{50}$ ($\mu$ g/ml) |
|---|---|---|
| R=H | (2S, 3R)-3-amino-2-hydroxy-4-phenyl-butanoyl-(S)-arginine hydrochloride | 0.03 |
| R=p-OH | (2S, 3R)-3-amino-2-hydroxy-4-p-hydroxy-phenylbutanoyl-(S)-arginine diacetate | 0.005 |
| R=p-Me | (2RS, 3Rs)-3-amino-2-hydroxy-4-p-methyl-phenylbutanoyl-(S)-arginine diacetate | 0.013 |
| R=o-Cl | (2RS, 3RS)-3-amino-2-hydroxy-4-o-chloro-phenylbutanoyl-(S)-arginine dihydrochloride | 0.14 |
| Bestatin | (control) | 0.10 |

As apparent from the results of the above table, the compounds (I) of this invention have far stronger inhibitory activity against aminopeptidase B than Bestatin (tested as control), corroborating the fact that the compounds (I) of this invention have excellent physiological activities.

(B) Effects of (2S,3R)-3-amino-2-hydroxy-4-phenylbutanoyl-(S)-arginine and (2S,3R)-3-amino-2-hydroxy-4-p-hydroxyphenylbutanoyl-(S)-arginine on lymphocyte blastoid transformation with phytohemagglutinin (PHA)

Method:

Lymphocytes were prepared asptically from the peripheral blood of healthy canines (Beagle, Male) by gradient centrifugation of ficollsodium metriazoate. The lymphocytes ($1 \times 10^6$ cells/ml) were cultured in RPMI-1640 medium with 10% fetal calf serum, antibiotic (Kanamycin 60$\mu$g/ml) and 15$\mu$g of phytohemagglutinin(PHA) at 37° C. in a humidified atomosphere of 5% $CO_2$ and 95% air. After an incubation for 48 hrs, 2$\mu$Ci of $^3$H-Thymidine was added to each dish, and the culture was continued for further 24 hrs to determine DNA synthesis. DNA synthesis was measured as $^3$H-

Thymidine incorporation into acid in soluble materials.

Table 2

| Compound | Dose (μg) | $^3$H-Tdη incorporation (mean cpm ± SE) |
| --- | --- | --- |
| PHA no treatment | — | 1173 ± 144 |
| PHA treatment | — | 16080 ± 1440 |
| PHA + bestatin | 0.1 | 19450 ± 189 |
| | 1.0 | 16173 ± 631 |
| | 10.0 | 18683 ± 71 |
| PHA + (2S,3R)-3-amino-2-hydroxy-4-phenyl-butanoyl-(S)-arginine . HCl | 0.1 | 17278 ± 400 |
| | 1.0 | 19940 ± 1412 |
| | 10.0 | 19050 ± 1988 |
| PHA + (2S,3R)-3-amino-2-hydroxy-4-p-hydroxy-phenylbutanoyl-(S)-arginine . 2 AcOH | 0.1 | 23113 ± 1236 |
| | 1.0 | 21357 ± 578 |
| | 10.0 | 20397 ± 304 |

Results:

As shown in table 2, bestatin, (2S,3R)-3-amino-2-hydroxy-4-phenylbutanoyl-(S)-arginine and (2S,3R)-3-amino-2-hydroxy-4-p-hydroxyphenylbutanoyl-(S)-arginine enhance the lymphocyte blastoid formation with PHA.

These results suggest the stimulation of immune mechanism of lymphocytes against tumor by these compounds, and the usefulness of these compounds as immune stimulators.

Now the process for the preparation of the compounds (I) of this invention is described by way of examples.

DESCRIPTION OF THE PREFERRED EMBODIMENTS

Example 1

Synthesis of (2S, 3R)-3-amino-2-hydroxy-4-phenylbutanoyl-(S)-arginine hydrochloride A solution prepared by dissolving 5.27 gr (25 mmoles) of (S)-arginine hydrochloride and 3.5 ml (25 mmoles) of triethylamine in 30 ml of water is added dropwise into 50 ml dioxane solution of 10.67 gr (25 mmoles) of N-hydroxysucciniimide ester of N-benzyloxycarbonyl-(2S, 3R)-3-amino-2-hydroxy-4-phenyl-butanoic acid over the period of about 3 hours. After 2-day reaction at room temperature, the solvent is distilled and the residue is dissolved in a 1:2 (by volume) chloroform/methanol solution and then subjected to column chromatography using Silicagel H Type 60 (Merck Corp.) to obtain the desired oily N-benzyloxycarbonyl-(2S, 3R)-3-amino-2-hydroxy-4-phenylbutanoyl-(S)-arginine hydrochloride. Yield: 5.74 gr.

This product is dissolved in a methanol (100 ml) and water (50 ml) mixture and subjected to a 6-hour catalytic reduction by using palladium black as catalyst.

After filtering off the catalyst, the solution is evaporated to dryness and the residue is collected with acetone, whereby 3.10 gr of (2S, 3R)-3-amino-2-hydroxy-4-phenylbutanoyl-(S)-arginine hydrochloride is obtained.

$[\alpha]_{578}^{32}$ −6.5° (c 1.2, AcOH), Rf 0.08 (measured on a silica-gel 60 F$_{254}$ plate (0.25 mm) (Merck Corp.) by using an n-BuOH/AcOH/H$_2$O (4:1:1) mixture as developing solvent). This substance is positive when tested in the color reactions with ninhydrin and Sakaguchi's reagent. Anal. Calcd. for C$_{16}$H$_{26}$O$_4$N$_5$Cl: C, 49.52; H, 6.76; N, 18.06. Found: C, 50.11; H, 6.92; N; N, 17.56.

Example 2

Synthesis of (2S, 3R)-3-amino-2-hydroxy-4-p-hydroxyphenylbutanoyl-(S)-arginine diacetate 345 mg of N-benzyloxycarbonyl-(2S, 3R)-3-amino-2-hydroxy-4-hydroxyphenylbutanoic acid, 783 mg of N$^G$-nitro-(S)-argininebenzylester.2p-toluenesulfonate and 162 mg of N-hydroxybenztriazole are dissolved in 20 ml of tetrahydrofuran, and after adjusting pH to 7.5 with 0.34 ml of triethylamine, there is added to said solution 206 mg of dicyclohexylcarbodiimide at 0° to 5° C. and the mixture is reacted overnight at the same temperature.

The reaction solution is concentrated and added with 50 ml of ethyl acetate, and the insolubles are filtered off. The ethyl acetate layer is washed with 0.5 N sulfuric acid solution, 2% sodium bicarbonate solution and water in this order. It is then dried with anhydrous magnesium sulfate, and after filtering off magnesium sulfate, the residue is concentrated under reduced pressure.

The obtained hygroscopic oily substance is dissolved in 10 ml methanol, 10 ml acetic acid and 10 ml water and then subjected to a 15-hour catalytic reduction in an autoclave at 30° C. and under 50 atm.

After filtering off the catalyst, the solution is evaporated to dryness under reduced pressure and the residue is subjected to preparative thin layer chromatography with Silicagel 60 F$_{254}$ plate (0.5 mm) (Merck Corp.) using an n-BuOH/AcOH/H$_2$O (4:1:1)) mixture as developing solvent. There is obtained the intended product in the yield of 140 mg. $[\alpha]_{578}^{27}$+2.6° (c 0.55, AcOH), Rf 0.07 (measured by using Silicagel 60 F$_{254}$ plate (0.25 mm) (Merck Corp.) and an n-BuOH/AcOH/H$_2$O (4:1:1) mixture as developing solvent).

This product is positive in the color reactions with ninhydrin, Sakaguchi's reagent and α-nitroso-β-naphthol/nitric acid. Anal. Calcd. for C$_{16}$H$_{26}$O$_5$N$_5$.2CH$_3$COOH.H$_2$O: C, 47.49; H, 6.98; N, 13.86. Found: C, 47.12; H, 7.08; N, 13.44.

Example 3

Synthesis of (2RS, 3RS)-3-amino-2-hydroxy-4-p-methylphenylbutanoyl-(S)-arginine diacetate 1.25 gr of dicyclohexylamine salt of N-benzyloxycarbonyl-(2RS, 3RS)-3-amino-2-hydroxy-4-p-methylphenylbutanoic acid (J. Med. Chem., 20 510 (1977)) is suspended in 50 ml of ethyl acetate and then shaken with 3 ml of 1 N H$_2$SO$_4$, followed by liquid separation. The ethyl acetate layer is washed with water, dried over anhydrous magnesium sulfate and concentrated under reduced pressure, producing oily N-benzyloxycarbonyl-(2RS, 3RS)-3-amino-2-hydroxy-4-p-methylphenylbutanoic acid. This oily substance is dissolved together with 1.57 gr of N$^G$-nitro-(S)-argininebenzylester.2-p-toluenesulfonate, 324 mg of N-hydroxybenztriazole and 0.67 ml of triethylamine in 20 ml of tetrahydrofuran, and after adding 412 mg of dicyclohexylcarbodiimide under ice cooling, the mixed solution is reacted overnight at the same temperature.

The reaction solution is concentrated under reduced pressure and added with 50 ml of ethyl acetate, followed by filter-off of the insolubles.

The ethyl acetate layer is washed with 0.5 N H$_2$SO$_4$, water, 2% NaHCO$_3$ solution and water in this order and then dried with anhydrous magnesium sulfate. After filtering off magnesium sulfate and distilling off the solvent under reduced pressure, the residue is refined by subjecting it to column chromatography with Silicagel H Type 60 (Merck Corp.) using ethyl acetate and methanol as developing solvent.

The obtained oily substance is dissolved in 5 ml methanol and 5 ml acetic acid and subjected to a 10-hour catalytic reduction at 25° C. under 50 atm.

After filtering off the catalyst and distilling off the solvent under reduced pressure, the residue is dissolved in 5 ml of water and then freeze-dried, whereby there is obtained the desired (2RS, 3RS)-3-amino-2-hydroxy-4-p-methylphenylbutanoyl(S)-arginine diacetate in the yield of 861 mg. $[\alpha]_{578}^{30}+4.5°$ (c 1.1, AcOH). Rf 0.07 (measured by using Silicagel 60 $F_{254}$ plate (0.25 mm) (Merck Corp.) and an n-BuOH/AcOH/$H_2O$ (4:1:1) mixture as developing solvent). Electrophoresis (AVICEL, 5 mA, 800 V, 10 min., pH 1.6, NCOOH: AcOH:$H_2O$=25:75:900) of this product gives a single spot with ninhydrin and Sakaguchi's reagent. Anal. Calcd. for $C_{17}H_{27}O_4N_5.2CH_3COOH.2H_2O$: C, 48.34; H, 7.54; N, 13.43. Found: C, 48.01; H, 7.77; N, 12.99.

Example 4

Synthesis of (2RS, 3RS)-3-amino-2-hydroxy-4-o-chlorophenylbutanoyl-(S)-arginine dihydrochloride 2.29 gr of (2RS, 3RS)-3-amino-2-hydroxy-4-o-chlorophenylbutanoic acid (J. Med. Chem., 20, 510 (1977)), 3.05 gr of tert-butyloxycarbonyl-S-4,6-dimethylpyrimidine-2-yl-thiolcarbonate and 2.1 ml of triethylamine are mixed and reacted in 20 ml of dioxane and 20 ml of water overnight at room temperature under agitation.

The solvent is distilled off to half volume and washed with 20 ml of ethyl acetate. The water layer is adjusted to pH 1 with 1 N $H_2SO_4$ and the precipitated oily substance is extracted with 100 ml of ethyl acetate. This is followed by washing with water, drying over anhydrous magnesium sulfate and concentration under reduced pressure to obtain an oily product.

2.44 gr of this N-tert-butyloxycarbonyl-(2RS, 3RS)-3-amino-2-hydroxy-4-o-chlorophenylbutanoic acid is dissolved in 20 ml ethyl acetate and 20 ml dioxane, and after adding 1.02 gr of N-hydroxysuccinimide, the mixed solution is cooled below $-5°$ C. After further addition of 1.54 gr of dicyclohexylcarbodiimide, the mixed solution is allowed to stand under this cooled condition for 2 hours and then agitated overnight at 25° C. The resultantly formed precipitate is filtered off and the solvent is distilled off under reduced pressure.

The obtained oily substance is again dissolved in 20 ml of dioxane, and to this solution is added 5 ml of an aqueous solution of 1.55 gr of (S)-arginine hydrochloride and 2.07 ml of triethylamine for the period of 30 minutes, allowing the mixture to react overnight at room temperature, followed by distilling-off of the solvent under reduced pressure.

The residue is refined by Silicagel H Type 60 (Merck Corp.) column chromatography using an n-BuOH/AcOH/$H_2O$ (4:1:1) mixture as developing solvent, consequently obtaining N-tert-butyloxycarbonyl-(2RS, 3RS)-3-amino-2-hydroxy-4-o-chlorophenylbutanoyl-(S)-arginine hydrochloride in the form of an oily product.

This oily product is dissolved in 10 ml of ice-cooled 4 N hydrochloric acid/dioxane and 10 ml of trifluoroacetic acid, then agitated at room temperature for 1 hour and concentrated under reduced pressure. The resultant substance is added with anhydrous ether and allowed to stand until it is solidified. When the product is washed with ether and filtered, there is obtained (2RS, 3RS)-3-amino-2-hydroxy-4-o-chlorophenylbutanoyl(S)-arginine dihydrochloride in the yield of 1.09 gr. $[\alpha]_{578}^{28}+0.7°$ (c 1.1, AcOH), Rf 0.07 (measured by using Silicagel 60 $F_{254}$ plate (0.25 mm) (Merck Corp.) and n-BuOH/AcOH/$H_2O$ (4:1:1) mixture as developing solvent.

Electrophoresis (AVICEL, 5 mA, 800 V, 10 min., pH 1.6, HCOOH:AcOH:$H_2O$=25:75:900) of this product gave a single spot with ninhydrin and Sakaguchi's reagent. Anal. Calcd. for $C_{16}H_{24}O_4N_5Cl.2HCl.H_2O$: C, 40.27; H, 5.87; N, 14.69. Found: C, 40.02; H, 6.19; N, 14.11.

Referential Example 1

Synthesis of N-hydroxysuccinimide ester of N-benzyloxycarbonyl-(2S, 3R)-3-amino-2-hydroxy-4-phenylbutanoic acid 16.50 gr of N-benzyloxycarbonyl-(2S,3R)-3-amino-2-hydroxy-4-phenylbutanoic acid (J. Med. Chem., 20, 510 (1977)) and 6.33 gr of N-hydroxysuccinimide are dissolved in 150 ml of dioxane and 150 ml of ethyl acetate, and after cooling to $-10°$ C., to the mixed solution there is added 10.3 gr of dicyclohexylcarbodiimide. After 1-hour reaction at the same temperature, the reaction solution is allowed to stand at room temperature overnight and the produced dicyclohexylurea is filtered off. The solvent is distilled off and the resultant oily substance is solidified with petroleum ether and recrystallized with ethyl acetate/petroleum ether to obtain 18.36 gr of N-hydroxysuccinimide ester of N-benzyloxycarbonyl-(2S, 3R)-3-amino-2-hydroxy-4-phenylbutanoic acid. M.p.: 111°-112° C. $[\alpha]_{578}^{30}+35.4°$ (c 1.5, AcOH).

Referential Example 2

Synthesis of N-benzyloxycarbonyl-(2S, 3R)-3-amino-2-hydroxy-p-hydroxyphenylbutanoic acid (A): Synthesis of (2RS, 3R)-3-amino-2-hydroxy-4-p-hydroxyphenylbutanoic acid 30.0 gr of oily N-benzyloxycarbonyl-(2RS, 3R)-3-amino-2-hydroxy-4-p-hydroxyphenylbutyronitrile is dissolved in 200 ml of concentrated hydrochloric acid and 200 ml of dioxane, and after adding 17.20 gr of anisole, the mixed solution is refluxed under heating for 4 hours.

After distilling off dioxane under reduced pressure, the hydrochloric acid solution is washed with ether and the water layer is concentrated under reduced pressure and evaporated to dryness.

Then 300 ml of water is added to the residue, and after filtering off the insolubles, the same amount of acetone is added and pH of the solution is adjusted 5.5 with ammonia water.

The solution is left in a refrigerator overnight and the precipitated crystals are filtered off, providing 12.61 gr of (2RS, 3R)-3-amino-2-hydroxy-4-p-hydroxyphenylbutanoic acid. Rf 0.20. Anal. Calcd. for $C_{10}H_{12}NO_4$: C, 58.81; H, 5.92; N, 7.82. Found: C, 58.63; H, 5.99; N, 7.43.

(B): Synthesis of N-benzyloxycarbonyl-(2S, 3R)-3-amino-2-hydroxy-4-p-hydroxyphenylbutanoic acid 7.20 gr of (2RS, 3R)-3-amino-2-hydroxy-4-p-hydroxyphenylbutanoic acid is benzyloxycarbonylated according to a known method (T. Nagasawa et al., Bull. Chem. Soc. Japan, 46, 1269 (1973)) by using 11.21 gr of benzyl-S-4,6-dimethylpyrimidine-2-yl-thiolcarbonate and then crystallized as a dicyclohexylamine salt, whereby 15.28 gr of dicyclohexylamine salt of N-benzyloxycarbonyl-(2RS, 3R)-3-amino-2-hydroxy-4-p-hydroxyphenylbutanoic acid is obtained.

When 15.22 gr of the obtained crude dicyclohexylamine salt is recrystallized from methanol/ethyl acetate/petroleum ether, there is obtained as first crystals 3.20 gr of optically impure dicyclohexylamine salt of N-benzyloxycarbonyl-(2R, 3R)-3-amino-2-hydroxy-4-p-hydroxyphenylbutanoic acid.

The mother liquor is concentrated and evaporated to dryness, and the residue is precipitated three times from ethyl acetate/ether, producing 5.02 gr of optically pure dicyclohexylamine salt of N-benzyloxycarbonyl-(2S, 3R)-3-amino-2-hydroxy-4-p-hydroxyphenylbutanoic acid. M.p.: 121°–122° C.; $[\alpha]_{578}^{20}$ 49.9° (c 0.87, AcOH). Anal. Calcd. for $C_{30}H_{42}N_2O_6$: C, 69.46; H, 8.16; N, 6.17. Found: C, 69.81; H, 8.35; N, 6.42.

We claim:

1. A compound represented by the following formula:

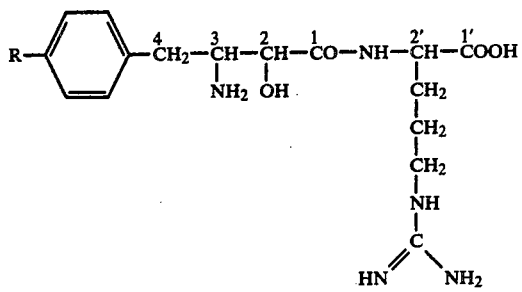

wherein R is hydrogen, hydroxy or alkyl having 1 to 4 carbon atoms and pharmaceutically acceptable acid addition salts thereof.

2. (2S, 3R)-3-amino-2-hydroxy-4-phenylbutanoyl-(S)-arginine.

3. (2S, 3R)-3-amino-2-hydroxy-4-p-hydroxyphenylbutanoyl-(S)-arginine.

4. (2RS, 3RS)-3-amino-2-hydroxy-4-p-methylphenylbutanoyl-(S)-arginine.

5. Compound of claim 1, wherein the acid addition salt is hydrochloride or acetate.

* * * * *